(12) United States Patent
Patel et al.

(10) Patent No.: US 8,053,393 B2
(45) Date of Patent: Nov. 8, 2011

(54) AQUEOUS HERBICIDAL COMPOSITION BASED ON A SUSPENSION CONCENTRATE COMPRISING HERBICIDES AND SAFENERS

(75) Inventors: Smita Patel, Eppstein-Bremthal (DE); Thomas Hannemann, Kriftel (DE); Tanja Weicke, Liederbach (DE)

(73) Assignee: Bayer CropScience AG, Monheim-Am-Rhein (DE)

( * ) Notice: Subject to any disclaimer, the term of this patent is extended or adjusted under 35 U.S.C. 154(b) by 1232 days.

(21) Appl. No.: 11/600,630

(22) Filed: Nov. 16, 2006

(65) Prior Publication Data

US 2007/0111890 A1    May 17, 2007

(30) Foreign Application Priority Data

Nov. 17, 2005  (EP) .................................... 05025149
Jun. 30, 2006   (DE) ......................... 10 2006 030 326

(51) Int. Cl.
*A01N 43/00*    (2006.01)

(52) U.S. Cl. ........................................................ 504/139

(58) Field of Classification Search .................. None
See application file for complete search history.

(56) References Cited

U.S. PATENT DOCUMENTS

| 6,884,757 B2 | 4/2005 | Ziemer et al. |
| 6,914,035 B2 | 7/2005 | Ziemer et al. |
| 2005/0233906 A1 | 10/2005 | Schnabel et al. |
| 2006/0240984 A1 | 10/2006 | Pallett et al. |
| 2008/0004180 A1* | 1/2008 | Dollinger et al. .............. 504/139 |

FOREIGN PATENT DOCUMENTS

| EP | 1023832 | * | 8/2000 |
| EP | 1 449 434 A | | 8/2004 |
| WO | WO-00/30447 A1 | | 6/2000 |
| WO | WO-01/17350 A | | 3/2001 |
| WO | WO-02/085120 A | | 10/2002 |
| WO | WO-03/022049 A1 | | 3/2003 |
| WO | WO-03/022050 A | | 3/2003 |
| WO | WO-03/026426 | | 4/2003 |
| WO | WO-03/026427 | | 4/2003 |
| WO | WO-2005/051082 A1 | | 6/2005 |
| WO | WO-2005/087004 | | 9/2005 |
| WO | WO-2005/087006 | | 9/2005 |
| ZA | 2001/3701 | | 2/2002 |
| ZA | 2002/1778 | | 12/2002 |
| ZA | 2004/2129 | | 6/2005 |
| ZA | 2004/2130 | | 7/2005 |

OTHER PUBLICATIONS

Tadros, Th.F., "Disperse Systems in Pesticidal Formulations," Advances in Colloid and Interface Science, Bd. 32, 1990, pp. 205-234.

Luckham, Paul F., "The Physical Stability of Suspension Concentrates with Particular Reference to Pharmaceutical and Pesticide Formulations," Pesticide Science, Elsevier Applied Science Publisher, Barking, Essex, GB, Bd. 25, Nr. 1, Jan. 1989, pp. 25-34.

* cited by examiner

Primary Examiner — Alton Pryor
(74) Attorney, Agent, or Firm — Connolly Bove Lodge & Hutz LLP

(57) ABSTRACT

The present invention relates to an aqueous herbicidal composition based on a suspension concentrate comprising
a herbicidally active compound of the formula (I),

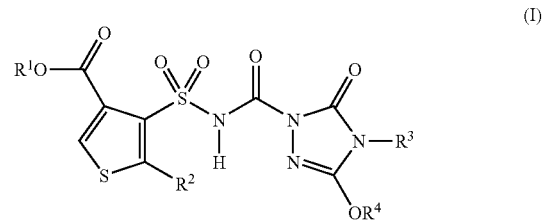

a safener of the formula (II)

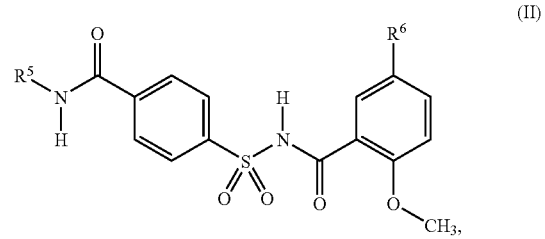

and optionally a herbicidally active compound of the formula (III)

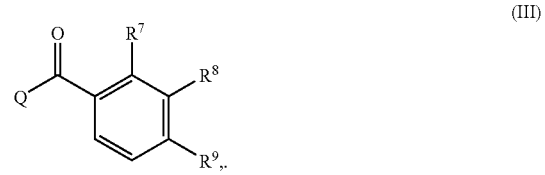

In these formulae, $R^1$, $R^2$, $R^3$ and $R^4$ independently of one another are methyl or ethyl; $R^5$ is isopropyl or cyclopropyl; $R^6$ is hydrogen or chlorine;
Q is cyclohexane-1,3-dion-2-yl, isoxazol-4-yl or pyrazol-4yl; and
$R^7$, $R^8$ and $R^9$ are hydrogen, halogen or various organic radicals.

18 Claims, No Drawings

AQUEOUS HERBICIDAL COMPOSITION BASED ON A SUSPENSION CONCENTRATE COMPRISING HERBICIDES AND SAFENERS

The present invention relates to the field of crop protection formulations. In particular, the invention relates to herbicidal compositions comprising at least one herbicidally active compound from the group of the inhibitors of acetolactate synthetase, a herbicidally active compound from the group of the inhibitors of hydroxyphenylpyruvate dioxygenase and at least one safener from the group of the acylsulfonamides, and formulations in the form of aqueous suspension concentrates comprising at least one herbicidally active compound from the group of the inhibitors of acetolactate synthetase and at least one safener from the group of the acylsulfonamides.

Herbicidally active compounds are generally not employed in their pure form. Depending on the area of use and the type of application, and on physical, chemical and biological parameters, the active compounds are employed as an active compound formulation in a mixture with customary auxiliaries and additives. Many herbicides display unwanted phytotoxic properties against useful plants. To increase the herbicidal activity against a large number of unwanted plants, the combined application of at least two herbicidally active compounds may be expedient. In some cases, this results in synergistic effects.

To avoid unwanted phytotoxic side-effects, it is known to apply herbicides in combination with a safener. Safeners are compounds which, fully or predominantly, prevent the phytotoxic side-effects of herbicides in useful plants.

Thus, WO 03/026427 discloses inter alia the mixtures of the herbicidally active compounds of the formula (I),

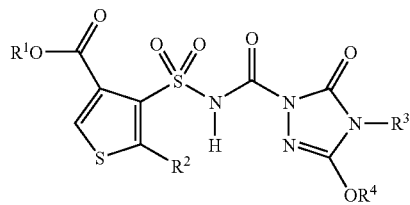

(I)

in which the radicals $R^1$ to $R^4$ are essentially alkyl, and safeners of the formula (II)

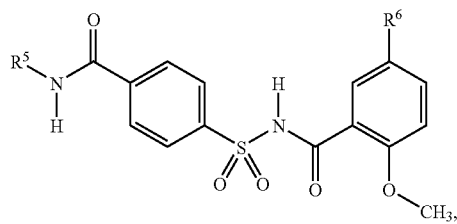

(II)

in which $R^5$ is essentially alkyl or cycloalkyl and $R^6$ is essentially hydrogen, alkyl or halogen.

Mixtures of the herbicidally active compounds of the formula (I) with other herbicidally active compounds, inter alia isoxaflutole, are known from WO 03/026426.

The combination of thiencarbazone-methyl, i.e. the compound of the formula (I) in which $R^1$ to $R^4$ are each methyl, with cyprosulfamide, i.e. the compound of the formula (II) in which $R^5$ is cyclopropyl and $R^6$ is hydrogen, and isoxaflutole, i.e. the compound of the formula (III) in which Q is $Q^2$, $R^7$ is methylsulfonyl, $R^8$ is hydrogen and $R^9$ is trifluoromethyl, is known from WO 2005/087006.

The combinations of a) thiencarbazone-methyl with cyprosulfamide and pyrasulfotole, i.e. the compound of the formula (III) in which Q is $Q^3$, $R^7$ is methylsulfonyl, $R^8$ is hydrogen and $R^9$ is trifluoromethyl, and b) thiencarbazone-methyl with cyprosulfamide and tembotrione, i.e. the compound of the formula (III) in which Q is $Q^1$, $R^7$ is chlorine, $R^8$ is 2,2,2-trifluoroethoxymethyl and $R^9$ is ethylsulfonyl, are known from WO 2005/087004.

All of the active compounds referred to above and below by their common name are also known, for example, from "The Pesticide Manual", 13th edition, The British Crop Protection Council and the Royal Soc. of Chemistry, 2003, and from the website http://www.hclrss.demon.co.uk.

The mixtures mentioned of herbicidally active compounds of the formula (I) and safeners of the formula (II) have good herbicidal activity, in particular for the control of unwanted plants in crops of corn; however, in practice they do not always have satisfactory properties, such as, for example, insufficient action against unwanted plants and/or lack of compatibility with useful plants, in particular in corn. Furthermore, for example, the storage stability of such mixtures is not always sufficient. The fact that, when the user dilutes the mixture to obtain a spray liquor, the two active compounds are not always homogeneously distributed therein, in particular when the mixture is not to be diluted in water, but in a concentrated aqueous solution of fertilizers, has to be considered a further disadvantage. Users increasingly demand the possibility for dilution in a concentrated aqueous solution of fertilizers.

It was an object of the present invention to provide a crop protection formulation of the herbicidally active compounds of the formula (I) in combination with safeners of the formula (II) and optionally a further herbicide from the group of the inhibitors of hydroxyphenylpyruvate dioxygenase, with these crop protection formulations having high storage stability and, after dilution with concentrated aqueous solutions of fertilizers, a homogeneous distribution of the active compounds.

This object is achieved by the special suspension concentrate of the present invention.

Accordingly, the present invention relates to an aqueous suspension concentrate, comprising A) a herbicidally active compound of the formula (I) (component A),

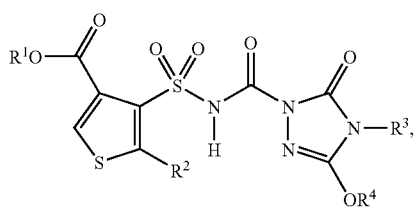

(I)

in which $R^1$, $R^2$, $R^3$ and $R^4$ independently of one another are methyl or ethyl, B) a safener of the formula (II) (component B),

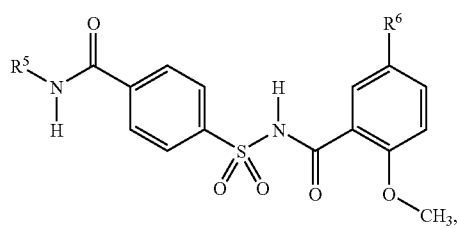

in which
R⁵ is isopropyl or cyclopropyl and
R⁶ is hydrogen or chlorine,
C) optionally a herbicidally active compound of the formula (III) (component C),

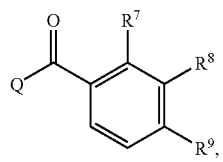

in which
Q is a radical Q¹, Q² or Q³,

Q¹
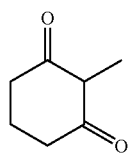

Q²
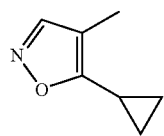

Q³
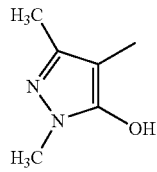

R⁷ is chlorine, methylsulfonyl or trifluoromethyl,
R⁸ is hydrogen or 2,2,2-trifluoroethoxymethyl,
R⁹ is methylsulfonyl or trifluoromethyl,
D) dispersants and
E) water.

Herbicidally active compounds of the formula (I) are known, for example, from WO 01/05788. Safeners of the formula (II) are known, for example, from U.S. Pat. No. 6,251,827. Herbicidally active compounds of the formula (III) in which Q is Q¹ are known, for example, from U.S. Pat. No. 6,376,429. Active compounds of the formula (III) in which Q is Q² are known, for example from EP 0 527 036. Active compounds of the formula (III) in which Q is Q³ are known, for example, from U.S. Pat. No. 6,420,317.

The aqueous suspension concentrates according to the invention have high storage stability and, on dilution with water or else with concentrated aqueous solutions of fertilizers, a homogeneous distribution of the active compounds, and do not tend to block spray nozzles.

The active compounds of the formulae (I), (II) and (III) in the suspension concentrates according to the invention may also be present in the form of their salts. Suitable salts are those described in the publications WO 01/05788, U.S. Pat. Nos. 6,251,827, 6,376,429, EP 0 527 036 and U.S. Pat. No. 6,420,317, in particular the alkali metal, alkaline earth metal and ammonium salts. Accordingly, unless indicated otherwise, in the present application the terms "herbicidally active compound of the formula (I)" or "formula (III)" and "safener of the formula (II)" are in each case meant to include both the pure compound and its respective salt, in particular the sodium salt.

The aqueous suspension concentrates according to the invention may additionally comprise further auxiliaries and additives customary in crop protection, in particular
F) antifreeze agents
G) preservatives
H) defoamers
I) thickeners and thixotropic agents.

In addition, they may also comprise further substances, such as colorants and fragrances, and antidrift agents, tackifiers and penetrants, evaporation inhibitors, and also agents for adjusting the pH and the viscosity.

Suitable dispersants are, for example, ionic and nonionic dispersants, for example:
1) tristyrylphenol polyethylene glycol phosphoric esters, for example Dispergon® LFH (Clariant), CAS No. 114535-82-9,
2) alkyl polyglycosides, such as $C_9$- to $C_{11}$-alkyl glucopyranosides, for example those of the Agniqu® PG series 9116 (Cognis),
3) alkyl polyglucosides, for example AL 2575 (Uniqema), CAS No. 68515-73-1.

The total proportion of dispersants in the suspension concentrates according to the invention is generally between 0.5 and 20% by weight. If the dispersants, in addition to their dispersing properties, are also used for increasing the biological effectiveness, for example as penetrants or tackifiers, their proportion in the suspension concentrates according to the invention may increase to up to 30% by weight.

Suitable antifreeze agents are those from the group of the ureas, diols and polyols, such as ethylene glycol and propylene glycol. The proportion of antifreeze agents in the suspension concentrates according to the invention is generally between 1 and 15% by weight, in particular between 2 and 10% by weight.

Suitable preservatives are those from the group of the isothiazoles, such as 2-methyl-2H-isothiazol-3-one, 1,2-benzisothiazol-3(2H)-one and the sodium salt. The proportion of preservatives in the suspension concentrates according to the invention is generally between 0.05 and 1% by weight, in particular between 0.05 and 0.5% by weight.

Suitable defoamers are, for example, those based on silicones, in particular polydimethylsiloxanes, preferably Rhodorsil® 481. The proportion of defoamers in the suspension concentrates according to the invention is generally between 0.05 and 1% by weight, in particular between 0.1 and 0.5% by weight.

Suitable thickeners and thixotropic agents are, for example:
1) modified natural silicates, such as chemically modified bentonites, hectorites, attapulgites, montmorillonites, smectites or other silicate minerals, such as Bentonee® (Elementis), Attagel® (Engelhard), Agsorb® (Oil-Dri Corporation) or Hectorite® (Akzo Nobel),
2) natural and synthetic silicates, such as silicates of the Sipernat®, Aerosil® or Durosil® series (Degussa), the CAB-O-SIL® series (Cabot) or the Van Gel series (R. T. Vanderbilt),
3) thickeners based on synthetic polymers, such as thickeners of the Thixin® or Thixatrol® series (Elementis).

Preferred thickeners and thixotropic agents are, for example, modified phyllosilicates and natural and synthetic silicates. The proportion of thickeners and thixotropic agents in the suspension concentrates according to the invention is generally between 0.1 and 5% by weight, in particular between 0.2 and 3% by weight.

Colorants and fragrances are known to the person skilled in the art.

Depending on the intended use, i.e. depending on which harmful plants are to be controlled in the crop plants in question, the aqueous suspension concentrates according to the invention also comprise a further agrochemically active compound, preferably from the group of the herbicides. This further herbicidally active compound may both be present in the aqueous suspension concentrate according to the invention as a ready formulation and be applied as a tank mix by joint dilution of the separately formulated or partially separately formulated components.

Particularly suitable for the aqueous suspension concentrates according to the invention are the active compounds A1 to A16 of formula (1):

(I)

| No. | $R^1$ | $R^2$ | $R^3$ | $R^4$ |
|---|---|---|---|---|
| A1 | ethyl | ethyl | ethyl | ethyl |
| A2 | ethyl | ethyl | ethyl | methyl |
| A3 | ethyl | ethyl | methyl | ethyl |
| A4 | ethyl | methyl | ethyl | ethyl |
| A5 | methyl | ethyl | ethyl | ethyl |
| A6 | ethyl | ethyl | methyl | methyl |
| A7 | methyl | ethyl | ethyl | methyl |
| A8 | methyl | methyl | ethyl | ethyl |
| A9 | ethyl | methyl | ethyl | methyl |
| A10 | methyl | ethyl | methyl | ethyl |
| A11 | ethyl | methyl | methyl | ethyl |
| A12 | methyl | methyl | methyl | methyl |
| A13 | methyl | methyl | methyl | ethyl |
| A14 | methyl | methyl | ethyl | methyl |
| A15 | methyl | ethyl | methyl | methyl |
| A16 | ethyl | methyl | methyl | methyl |

Particularly suitable for the aqueous suspension concentrates according to the invention are the active compounds B1 to B4 of formula (II):

(II)

| No. | $R^5$ | $R^6$ |
|---|---|---|
| B1 | isopropyl | hydrogen |
| B2 | isopropyl | chlorine |
| B3 | cyclopropyl | hydrogen |
| B4 | cyclopropyl | chlorine |

Particularly suitable for the aqueous suspension concentrates according to the invention are the active compounds C1 to C3 of formula (III):

(III)

| No. | Q | $R^7$ | $R^8$ | $R^9$ |
|---|---|---|---|---|
| C1 | (2-methylcyclohexane-1,3-dione) | Cl | $CH_2OCH_2CF_3$ | $SO_2CH_3$ |
| C2 | (4-methyl-5-cyclopropylisoxazole) | $SO_2CH_3$ | H | $CF_3$ |
| C3 | (1,3-dimethyl-4-methyl-5-hydroxypyrazole) | $SO_2CH_3$ | H | $CF_3$ |

Suspension concentrates according to the invention comprising the components A and B or A, B and C mentioned below may be mentioned as preferred examples, without this constituting a limitation.

| A1 + B1 | A2 + B1 | A3 + B1 | A4 + B1 | A5 + B1 | A6 + B1 |
| A7 + B1 | A8 + B1 | A9 + B1 | A10 + B1 | A11 + B1 | A12 + B1 |
| A13 + B1 | A14 + B1 | A15 + B1 | A16 + B1 | A1 + B2 | A2 + B2 |
| A3 + B2 | A4 + B2 | A5 + B2 | A6 + B2 | A7 + B2 | A8 + B2 |

-continued

| | | | | | |
|---|---|---|---|---|---|
| A9 + B2 | A10 + B2 | A11 + B2 | A12 + B2 | A13 + B2 | A14 + B2 |
| A15 + B2 | A16 + B2 | A1 + B3 | A2 + B3 | A3 + B3 | A4 + B3 |
| A5 + B3 | A6 + B3 | A7 + B3 | A8 + B3 | A9 + B3 | A10 + B3 |
| A11 + B3 | A12 + B3 | A13 + B3 | A14 + B3 | A15 + B3 | A16 + B3 |
| A1 + B4 | A2 + B4 | A3 + B4 | A4 + B4 | A5 + B4 | A6 + B4 |
| A7 + B4 | A8 + B4 | A9 + B4 | A10 + B4 | A11 + B4 | A12 + B4 |
| A13 + B4 | A14 + B4 | A15 + B4 | A16 + B4 | | |
| A1 + B1 + C1 | A1 + B2 + C1 | A1 + B3 + C1 | A1 + B4 + C1 | | |
| A1 + B1 + C2 | A1 + B2 + C2 | A1 + B3 + C2 | A1 + B4 + C2 | | |
| A1 + B1 + C3 | A1 + B2 + C3 | A1 + B3 + C3 | A1 + B4 + C3 | | |
| A2 + B1 + C1 | A2 + B2 + C1 | A2 + B3 + C1 | A2 + B4 + C1 | | |
| A2 + B1 + C2 | A2 + B2 + C2 | A2 + B3 + C2 | A2 + B4 + C2 | | |
| A2 + B1 + C3 | A2 + B2 + C3 | A2 + B3 + C3 | A2 + B4 + C3 | | |
| A3 + B1 + C1 | A3 + B2 + C1 | A3 + B3 + C1 | A3 + B4 + C1 | | |
| A3 + B1 + C2 | A3 + B2 + C2 | A3 + B3 + C2 | A3 + B4 + C2 | | |
| A3 + B1 + C3 | A3 + B2 + C3 | A3 + B3 + C3 | A3 + B4 + C3 | | |
| A4 + B1 + C1 | A4 + B2 + C1 | A4 + B3 + C1 | A4 + B4 + C1 | | |
| A4 + B1 + C2 | A4 + B2 + C2 | A4 + B3 + C2 | A4 + B4 + C2 | | |
| A4 + B1 + C3 | A4 + B2 + C3 | A4 + B3 + C3 | A4 + B4 + C3 | | |
| A5 + B1 + C1 | A5 + B2 + C1 | A5 + B3 + C1 | A5 + B4 + C1 | | |
| A5 + B1 + C2 | A5 + B2 + C2 | A5 + B3 + C2 | A5 + B4 + C2 | | |
| A5 + B1 + C3 | A5 + B2 + C3 | A5 + B3 + C3 | A5 + B4 + C3 | | |
| A6 + B1 + C1 | A6 + B2 + C1 | A6 + B3 + C1 | A6 + B4 + C1 | | |
| A6 + B1 + C2 | A6 + B2 + C2 | A6 + B3 + C2 | A6 + B4 + C2 | | |
| A6 + B1 + C3 | A6 + B2 + C3 | A6 + B3 + C3 | A6 + B4 + C3 | | |
| A7 + B1 + C1 | A7 + B2 + C1 | A7 + B3 + C1 | A7 + B4 + C1 | | |
| A7 + B1 + C2 | A7 + B2 + C2 | A7 + B3 + C2 | A7 + B4 + C2 | | |
| A7 + B1 + C3 | A7 + B2 + C3 | A7 + B3 + C3 | A7 + B4 + C3 | | |
| A8 + B1 + C1 | A8 + B2 + C1 | A8 + B3 + C1 | A8 + B4 + C1 | | |
| A8 + B1 + C2 | A8 + B2 + C2 | A8 + B3 + C2 | A8 + B4 + C2 | | |
| A8 + B1 + C3 | A8 + B2 + C3 | A8 + B3 + C3 | A8 + B4 + C3 | | |
| A9 + B1 + C1 | A9 + B2 + C1 | A9 + B3 + C1 | A9 + B4 + C1 | | |
| A9 + B1 + C2 | A9 + B2 + C2 | A9 + B3 + C2 | A9 + B4 + C2 | | |
| A9 + B1 + C3 | A9 + B2 + C3 | A9 + B3 + C3 | A9 + B4 + C3 | | |
| A10 + B1 + C1 | A10 + B2 + C1 | A10 + B3 + C1 | A10 + B4 + C1 | | |
| A10 + B1 + C2 | A10 + B2 + C2 | A10 + B3 + C2 | A10 + B4 + C2 | | |
| A10 + B1 + C3 | A10 + B2 + C3 | A10 + B3 + C3 | A10 + B4 + C3 | | |
| A11 + B1 + C1 | A11 + B2 + C1 | A11 + B3 + C1 | A11 + B4 + C1 | | |
| A11 + B1 + C2 | A11 + B2 + C2 | A11 + B3 + C2 | A11 + B4 + C2 | | |
| A11 + B1 + C3 | A11 + B2 + C3 | A11 + B3 + C3 | A11 + B4 + C3 | | |
| A12 + B1 + C1 | A12 + B2 + C1 | A12 + B3 + C1 | A12 + B4 + C1 | | |
| A12 + B1 + C2 | A12 + B2 + C2 | A12 + B3 + C2 | A12 + B4 + C2 | | |
| A12 + B1 + C3 | A12 + B2 + C3 | A12 + B3 + C3 | A12 + B4 + C3 | | |
| A13 + B1 + C1 | A13 + B2 + C1 | A13 + B3 + C1 | A13 + B4 + C1 | | |
| A13 + B1 + C2 | A13 + B2 + C2 | A13 + B3 + C2 | A13 + B4 + C2 | | |
| A13 + B1 + C3 | A13 + B2 + C3 | A13 + B3 + C3 | A13 + B4 + C3 | | |
| A14 + B1 + C1 | A14 + B2 + C1 | A14 + B3 + C1 | A14 + B4 + C1 | | |
| A14 + B1 + C2 | A14 + B2 + C2 | A14 + B3 + C2 | A14 + B4 + C2 | | |
| A14 + B1 + C3 | A14 + B2 + C3 | A14 + B3 + C3 | A14 + B4 + C3 | | |
| A15 + B1 + C1 | A15 + B2 + C1 | A15 + B3 + C1 | A15 + B4 + C1 | | |
| A15 + B1 + C2 | A15 + B2 + C2 | A15 + B3 + C2 | A15 + B4 + C2 | | |
| A15 + B1 + C3 | A15 + B2 + C3 | A15 + B3 + C3 | A15 + B4 + C3 | | |
| A16 + B1 + C1 | A16 + B2 + C1 | A16 + B3 + C1 | A16 + B4 + C1 | | |
| A16 + B1 + C2 | A16 + B2 + C2 | A16 + B3 + C2 | A16 + B4 + C2 | | |
| A16 + B1 + C3 | A16 + B2 + C3 | A16 + B3 + C3 | A16 + B4 + C3 | | |

Preference is also given to aqueous suspension concentrates according to the invention of the abovementioned combinations of the active compounds A and B or A, B and C in each case as a mixture with one or more dispersants from the group consisting of tristyrylphenol polyethylene glycol phosphoric esters, alkyl polyglycosides and alkyl polyglucosides.

In a preferred embodiment, the aqueous suspension concentrates according to the invention comprise A) from 4 to 30% of a herbicidally active compound A1 to A16 of the formula (I),
B) from 4 to 30% of a safener B1 to B4 of the formula (II),
C) from 0 to 35% of a herbicidally active compound C1 to C3 of the formula (III),
D) from 0.5 to 30% of one or more dispersants,
E) from 30 to 70% of water,
F) from 1 to 15% of one or more antifreeze agents,
G) from 0.05 to 1% of one or more preservatives,
H) from 0.05 to 1% of one or more defoamers,
I) from 0.1 to 5% of one or more thickeners or thixotropic agents.

Particular preference is given to aqueous suspension concentrates according to the invention comprising A) from 5 to 25% of a herbicidally active compound A1 to A16 of the formula (I),
B) from 5 to 25% of a safener B1 to B4 of the formula (II),
C) from 0 to 30% of a herbicidally active compound C1 to C3 of the formula (III),
D) from 1 to 20% of one or more dispersants,
E) from 35 to 65% of water,
F) from 2 to 10% of one or more antifreeze agents,
G) from 0.05 to 0.5% of one or more preservatives,
H) from 0.1 to 1% of one or more defoamers,
I) from 0.2 to 3% of one or more thickeners or thixotropic agents.

Very particular preference is given to aqueous suspension concentrates according to the invention comprising
A) from 5 to 20% of a herbicidally active compound A1 to A16, in particular A12, of the formula (I),
B) from 8 to 20% of a safener B1 to B4, in particular B3, of the formula (II),
C) from 0 to 25% of a herbicidally active compound C1 to C3, in particular C2, of the formula (III),
D) from 2.5 to 15% of one or more dispersants,
E) from 40 to 60% of water,
F) from 2 to 10% of one or more antifreeze agents,
G) from 0.05 to 0.25% of one or more preservatives,
H) from 0.1 to 0.5% of one or more defoamers,
I) from 0.25 to 2.5% of one or more thickeners or thixotropic agents.

All percentages are percent by weight.

Combinations of the active compounds of the formulae (I), (II) and (III), except for the combinations of
a) thiencarbazone-methyl, cyprosulfamide and tembotrione,
b) thiencarbazone-methyl, cyprosulfamide and isoxaflutole, and
c) thiencarbazone-methyl, cyprosulfamide and pyrasulfotole,
are per se novel and also form part of the subject matter of the invention. These combinations are highly suitable for use as herbicidal compositions. Particularly suitable for use as herbicidal compositions are those comprising the components A, B and C of the following list:

| | | | |
|---|---|---|---|
| A1 + B1 + C1 | A1 + B2 + C1 | A1 + B3 + C1 | A1 + B4 + C1 |
| A1 + B1 + C2 | A1 + B2 + C2 | A1 + B3 + C2 | A1 + B4 + C2 |
| A1 + B1 + C3 | A1 + B2 + C3 | A1 + B3 + C3 | A1 + B4 + C3 |
| A2 + B1 + C1 | A2 + B2 + C1 | A2 + B3 + C1 | A2 + B4 + C1 |
| A2 + B1 + C2 | A2 + B2 + C2 | A2 + B3 + C2 | A2 + B4 + C2 |
| A2 + B1 + C3 | A2 + B2 + C3 | A2 + B3 + C3 | A2 + B4 + C3 |
| A3 + B1 + C1 | A3 + B2 + C1 | A3 + B3 + C1 | A3 + B4 + C1 |
| A3 + B1 + C2 | A3 + B2 + C2 | A3 + B3 + C2 | A3 + B4 + C2 |
| A3 + B1 + C3 | A3 + B2 + C3 | A3 + B3 + C3 | A3 + B4 + C3 |
| A4 + B1 + C1 | A4 + B2 + C1 | A4 + B3 + C1 | A4 + B4 + C1 |
| A4 + B1 + C2 | A4 + B2 + C2 | A4 + B3 + C2 | A4 + B4 + C2 |
| A4 + B1 + C3 | A4 + B2 + C3 | A4 + B3 + C3 | A4 + B4 + C3 |
| A5 + B1 + C1 | A5 + B2 + C1 | A5 + B3 + C1 | A5 + B4 + C1 |
| A5 + B1 + C2 | A5 + B2 + C2 | A5 + B3 + C2 | A5 + B4 + C2 |
| A5 + B1 + C3 | A5 + B2 + C3 | A5 + B3 + C3 | A5 + B4 + C3 |
| A6 + B1 + C1 | A6 + B2 + C1 | A6 + B3 + C1 | A6 + B4 + C1 |
| A6 + B1 + C2 | A6 + B2 + C2 | A6 + B3 + C2 | A6 + B4 + C2 |
| A6 + B1 + C3 | A6 + B2 + C3 | A6 + B3 + C3 | A6 + B4 + C3 |
| A7 + B1 + C1 | A7 + B2 + C1 | A7 + B3 + C1 | A7 + B4 + C1 |
| A7 + B1 + C2 | A7 + B2 + C2 | A7 + B3 + C2 | A7 + B4 + C2 |
| A7 + B1 + C3 | A7 + B2 + C3 | A7 + B3 + C3 | A7 + B4 + C3 |
| A8 + B1 + C1 | A8 + B2 + C1 | A8 + B3 + C1 | A8 + B4 + C1 |
| A8 + B1 + C2 | A8 + B2 + C2 | A8 + B3 + C2 | A8 + B4 + C2 |
| A8 + B1 + C3 | A8 + B2 + C3 | A8 + B3 + C3 | A8 + B4 + C3 |
| A9 + B1 + C1 | A9 + B2 + C1 | A9 + B3 + C1 | A9 + B4 + C1 |
| A9 + B1 + C2 | A9 + B2 + C2 | A9 + B3 + C2 | A9 + B4 + C2 |
| A9 + B1 + C3 | A9 + B2 + C3 | A9 + B3 + C3 | A9 + B4 + C3 |
| A10 + B1 + C1 | A10 + B2 + C1 | A10 + B3 + C1 | A10 + B4 + C1 |
| A10 + B1 + C2 | A10 + B2 + C2 | A10 + B3 + C2 | A10 + B4 + C2 |
| A10 + B1 + C3 | A10 + B2 + C3 | A10 + B3 + C3 | A10 + B4 + C3 |
| A11 + B1 + C1 | A11 + B2 + C1 | A11 + B3 + C1 | A11 + B4 + C1 |
| A11 + B1 + C2 | A11 + B2 + C2 | A11 + B3 + C2 | A11 + B4 + C2 |
| A11 + B1 + C3 | A11 + B2 + C3 | A11 + B3 + C3 | A11 + B4 + C3 |
| A12 + B1 + C1 | A12 + B2 + C1 | A12 + B4 + C1 | |
| A12 + B1 + C2 | A12 + B2 + C2 | A12 + B4 + C2 | |
| A12 + B1 + C3 | A12 + B2 + C3 | A12 + B4 + C3 | |
| A13 + B1 + C1 | A13 + B2 + C1 | A13 + B3 + C1 | A13 + B4 + C1 |
| A13 + B1 + C2 | A13 + B2 + C2 | A13 + B3 + C2 | A13 + B4 + C2 |
| A13 + B1 + C3 | A13 + B2 + C3 | A13 + B3 + C3 | A13 + B4 + C3 |
| A14 + B1 + C1 | A14 + B2 + C1 | A14 + B3 + C1 | A14 + B4 + C1 |
| A14 + B1 + C2 | A14 + B2 + C2 | A14 + B3 + C2 | A14 + B4 + C2 |
| A14 + B1 + C3 | A14 + B2 + C3 | A14 + B3 + C3 | A14 + B4 + C3 |
| A15 + B1 + C1 | A15 + B2 + C1 | A15 + B3 + C1 | A15 + B4 + C1 |
| A15 + B1 + C2 | A15 + B2 + C2 | A15 + B3 + C2 | A15 + B4 + C2 |
| A15 + B1 + C3 | A15 + B2 + C3 | A15 + B3 + C3 | A15 + B4 + C3 |
| A16 + B1 + C1 | A16 + B2 + C1 | A16 + B3 + C1 | A16 + B4 + C1 |
| A16 + B1 + C2 | A16 + B2 + C2 | A16 + B3 + C2 | A16 + B4 + C2 |
| A16 + B1 + C3 | A16 + B2 + C3 | A16 + B3 + C3 | A16 + B4 + C3 |

Very particularly suitable are herbicidal compositions comprising the components

| | | | |
|---|---|---|---|
| A12 + B1 + C1 | A12 + B2 + C1 | A12 + B3 + C1 | A12 + B4 + C1 |
| A12 + B1 + C2 | A12 + B2 + C2 | | A12 + B4 + C2 |
| A12 + B1 + C3 | A12 + B2 + C3 | A12 + B3 + C3 | A12 + B4 + C3. |

The abovementioned formulation auxiliaries of groups d) and f) to i) are known to the person skilled in the art and are described, for example, in: Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte [Surface-active ethylene oxide adducts]", Wiss. Verlagsgesell., Stuttgart 1976; Winnacker-Küchler, "Chemische Technologie [Chemical technology]", volume 7, C. Hauser Verlag Munich, 4th Ed. 1986.

For use, the aqueous suspension concentrates or herbicidal compositions according to the invention can be diluted in a customary manner, for example with water or with aqueous solutions of fertilizers, such as ammonium hydrogensulfate. It may be advantageous to add, to the resulting spray liquors, further agrochemically active compounds (for example components for tank mixes in the form of suitable formulations) and/or customary auxiliaries and additives conventionally used for application and/or fertilizers. It has been found to be advantageous to dilute the aqueous suspension concentrates or herbicidal compositions according to the invention with aqueous solutions of fertilizers, for example ammonium nitrate and ammonium sulfate.

The present invention accordingly also provides those aqueous suspension concentrates or herbicidal compositions comprising the agrochemically active compounds, auxiliaries and additives and/or fertilizers mentioned in the above section.

The aqueous suspension concentrates and herbicidal compositions according to the invention have outstanding herbicidal activity against a broad spectrum of economically important monocotyledonous and dicotyledonous harmful plants. They even effect good control of perennial problem weeds which emerge from rhizomes, root stocks or other perennial organs.

The aqueous suspension concentrates and herbicidal compositions according to the invention have prolonged herbicidal activity with prompt onset.

Although the aqueous suspension concentrates and herbicidal compositions according to the invention have an outstanding herbicidal activity against monocotyledonous and dicotyledonous weeds, crop plants of economically important crops, for example dicotyledonous crops such as soybeans, cotton, oilseed rape, sugar beet, or graminaceous crops such as wheat, barley, rye, oats and millet, sugar cane, coffee, tea, cocoa, coconut, bananas or corn only suffer minor damage, if any. This is why the aqueous suspension concentrates and herbicidal compositions according to the invention are highly suitable for the selective control of unwanted vegetation in plantations of agriculturally useful crops, in particular in corn crops, or in ornamental plantations.

By virtue of their herbicidal properties, the aqueous suspension concentrates and herbicidal compositions according to the invention can also be employed for controlling harmful plants in crops of genetically modified plants which are known or yet to be developed. In general, the transgenic plants have specific advantageous properties, for example resistances to certain pesticides, especially certain herbicides, resistances to plant diseases or pathogens causing plant diseases, such as certain insects or microorganisms, such as fungi, bacteria or viruses. Other specific properties relate, for example, to quantity, quality, storability, composition and specific constituents of the harvested material. Thus, transgenic plants having an increased starch content or modified starch quality or else having a different fatty acid composition of the harvested material, are known.

Preferred is the use of the aqueous suspension concentrates and herbicidal compositions according to the invention in economically important transgenic crops of useful plants and ornamentals, for example graminaceous crops, such as wheat, barley, rye, oats, millet, rice and corn, in particular corn, or else crops of sugar beet, cotton, soybean, oilseed rape, potato, tomato, pea and other vegetables. The aqueous suspension concentrates and herbicidal compositions according to the invention can be employed as herbicides in crops of useful plants which are resistant, or which have been made resistant by means of genetic engineering, to the phytotoxic effects of the herbicidally active compounds.

When the aqueous suspension concentrates and herbicidal compositions according to the invention are applied in transgenic crops, effects are frequently observed which are specific for the application in the transgenic crop in question, for example a modified, or specifically broadened, spectrum of weeds which can be controlled, modified application rates which can be employed for the application, preferably good combining ability with the herbicides to which the transgenic crop is resistant, and an effect on the growth and yield of the transgenic crop plants, in addition to the effects, against harmful plants, which can be observed in the other crops.

The present invention furthermore also provides a method for controlling unwanted vegetation, preferably in crop plants such as cereals (for example wheat, barley, rye, oats, rice, corn, millet), sugar beet, sugar cane, oilseed rape, cotton and soybeans, particularly preferably in monocotyledonous crops, such as cereals, for example wheat, barley, rye, oats, their hybridization products, such as triticale, rice, corn and millet, one or more aqueous suspension concentrates or herbicidal compositions according to the invention being applied to the harmful plants, parts of plants, plant seeds or the area in which the plants grow, for example the area under cultivation.

The plant crops can also have been genetically modified or have been obtained by mutation selection and are preferably tolerant to acetolactate synthase (ALS) inhibitors.

The aqueous suspension concentrates according to the invention are prepared in a manner known to the person skilled in the art, for example by mixing the individual constituents; see, in this context, Winnacker-Küchler, "Chemische Technologie", volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The examples below illustrate the invention. The surfactants and auxiliaries used in this context mean:

Dispergon® LFH=tristyrylphenol polyethylene glycol phosphoric ester, supplier: CLARIANT
Agnique® PG 9116=$C_9$- to $C_{11}$-alkyl glucopyranoside, supplier: COGNIS
AL 2575=alkyl polyglucoside, supplier: UNIQEMA
Rhodorsil® 416=defoamer based on polydimethylsiloxane, supplier: RHODIA
Acticide® MBS=mixture of 2-methyl-2H-isothiazol-3-one and 1,2-benzisothiazol-3(2H)-one supplier: THOR
Proxel® GXL=sodium salt of 1,2-benzisothiazol-3(2H)-one supplier: ZENECA
Aerosil® 200=silicon dioxide, chemically obtained supplier: Degussa
Attagel® 50=magnesium aluminum hydrosilicate supplier: CHEMIE-MINERALIEN GMBH
VanGel® B=hydrated magnesium aluminum silicate supplier: VANDERBILT INC., ERBSLÖH KG

WORKING EXAMPLES

The preparation procedure described below relates to the recipes of examples 1 to 4 mentioned below:

Water is initially charged in a stirred tank. With stirring, defoamers, dispersants, preservatives and antifreeze agents, herbicides and safeners are added, and stirring is continued for a short while. Thickeners and thixotropic agents are then added. The suspension obtained in this manner is subjected to coarse pregrinding in a colloid mill and then ground in a glass bead mill using glass beads of a diameter of 1 mm until the mean particle size is 1 to 2 micron. During grinding, the suspension is kept at a temperature of at most 25° C. using external cooling.

EXAMPLE 1

| | | |
|---|---|---|
| A) | 7.95 g | herbicide A12 |
| B) | 13.16 g | safener B3 |
| C) | 19.32 g | herbicide C2 |
| D) | 3.00 g | Dispergon ® LFH |
| D) | 2.00 g | AL 2575 |
| E) | 46.57 g | water |
| F) | 7.00 g | propylene glycol |
| G) | 0.10 g | Proxel ® GXL |
| H) | 0.25 g | Rhodorsil ® 416 |
| I) | 0.65 g | Aerosil ® 200 |

EXAMPLE 2

| | | |
|---|---|---|
| A) | 7.95 g | herbicide A12 |
| B) | 13.16 g | safener B3 |
| C) | 19.32 g | herbicide C2 |
| D) | 3.00 g | Dispergon ® LFH |
| D) | 2.00 g | Agnique ® PG 9116 |
| E) | 46.57 g | water |
| F) | 7.00 g | propylene glycol |
| G) | 0.10 g | Proxel ® GXL |
| H) | 0.25 g | Rhodorsil ® 416 |
| I) | 0.65 g | Aerosil ® 200 |

EXAMPLE 3

| | | |
|---|---|---|
| A) | 20.21 g | herbicide A12 |
| B) | 20.08 g | safener B3 |
| D) | 3.00 g | Dispergon ® LFH |
| D) | 1.00 g | AL 2575 |
| E) | 47.36 g | water |
| F) | 7.00 g | propylene glycol |
| G) | 0.10 g | Proxel ® GXL |
| H) | 0.25 g | Rhodorsil ® 416 |

EXAMPLE 3-continued

| I) | 0.50 g | Attagel ® 50 |
|---|---|---|
| I) | 0.50 g | VanGel ® B |

EXAMPLE 4

| A) | 20.05 g | herbicide A12 |
|---|---|---|
| B) | 20.08 g | safener B3 |
| D) | 4.00 g | Dispergon ® LFH |
| D) | 1.00 g | AL 2575 |
| E) | 46.32 g | water |
| F) | 7.00 g | propylene glycol |
| G) | 0.10 g | Proxel ® GXL |
| H) | 0.25 g | Rhodorsil ® 416 |
| I) | 0.60 g | Attagel ® 50 |
| I) | 0.60 g | VanGel ® B |

After storage for several months even at elevated temperature, the aqueous suspension concentrates according to the invention have excellent stability and do not have any tendency to flocculate or to block spray nozzles.

WORKING EXAMPLES

Post-emergence Herbicidal Action

Seeds of monocotyledonous and dicotyledonous weeds and crop plants are placed in sandy loam in wood fiber pots or in plastic pots, covered with soil and grown in the greenhouse, during the vegetation period also outdoors outside of the greenhouse, under good growth conditions. 2 to 3 weeks after sowing, the test plants, which are in the one to three-leaf stage, are treated. The formulated herbicidal compositions are sprayed onto the plants and the soil surface in various dosages at a water application rate of 300 l/ha (converted), with addition of wetting agent (0.2 to 0.3%). 3 to 4 weeks after the treatment of the test plants, the effect of the preparations is scored visually in comparison to untreated controls (herbicidal activity in percent (%): 100% activity=the plants have died, 0% activity=like control plants).

Here, for example, the herbicidal compositions 1 to 4 exhibit, at an application rate of 320 g (sum of the three components A, B and C, in a ratio of 1:1.65:2.43) per hectar, at least 90% activity against numerous harmful plants, such as *Abutilon theophrasti, Alopecurus myosuroides, Amaranthus retroflexus, Avena fatua, Chenopodium album, Cyperus serotinus, Digitaria sanguinalis, Matricaria chamomilla, Setaria viridis* and *Veronica persica* and less than 5% damage of crop plants, such as corn.

| Herbicidal composition No. | Component | | |
|---|---|---|---|
| 1 | A12 | B3 | C2 |
| 2 | A12 | B1 | C2 |
| 3 | A14 | B3 | C2 |
| 4 | A14 | B1 | C2 |

The effect of the safener substance can be assessed by comparison of the activity of test substances on crop plants treated without and with safener.

Here, it is found that the herbicidal activities of the compositions according to the invention (100% and 99%, respectively) exceed the values expected according to Colby (in each case 85%) calculated using the formula below (cf. S. R. Colby; in Weeds 15 (1967) pp. 20 to 22):

$$E = A + B - \frac{A \times B}{100}$$

here:
A, B=activity of component A and B, respectively, in percent
E=expected value in percent

The invention claimed is:
1. An aqueous suspension concentrate, comprising
   A) a herbicidally active compound of formula (I) in suspended form

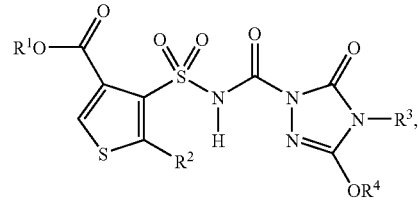

in which
   $R^1$, $R^2$, $R^3$ and $R^4$ independently of one another are methyl or ethyl,
   B) a safener of formula (II),

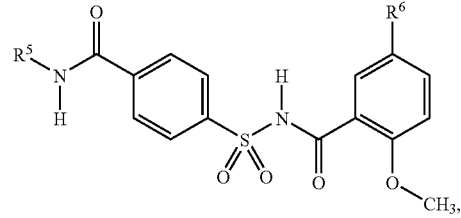

in which
   $R^5$ is isopropyl or cyclopropyl and
   $R^6$ is hydrogen or chlorine,
   C) dispersants comprising poly(oxy-1,2-ethanediyl), alpha-phosphono-omega-[2,4,6-tris(1-phenylethyl) phenoxy] and at least one other dispersant selected from the group consisting of alkyl polyglycosides and alkyl polyglucosides, and
   D) water.
2. The suspension concentrate as claimed in claim 1, additionally comprising:
   E) antifreeze agents;
   F) preservatives;
   G) defoamers; and
   H) thickeners.
3. An aqueous herbicidal composition, obtained by diluting a suspension concentrate as claimed in claim 1 with water.
4. An aqueous herbicidal composition, obtained by diluting a suspension concentrate as claimed in claim 1 with an aqueous solution of fertilizer.
5. The aqueous herbicidal composition as claimed in claim 4, wherein the fertilizer is ammonium sulfate or ammonium nitrate.
6. A method for controlling unwanted vegetation comprising applying an effective amount of an aqueous suspension concentrate as claimed in claim 1 to plants, parts of the plants, a seed or an area in which the plants grow.

7. An aqueous herbicidal composition obtained by diluting a herbicidal composition as claimed in claim 3 with an aqueous solution of fertilizer.

8. The suspension concentrate as claimed in claim 1, wherein the dispersants comprise poly(oxy-1,2-ethanediyl), alpha-phosphono-omega-[2,4,6-tris(1-phenylethyl)phenoxy], alkyl polyglycosides and alkyl polyglucosides.

9. The suspension concentrate as claimed in claim 1, further comprising a herbicidally active compound of formula (III),

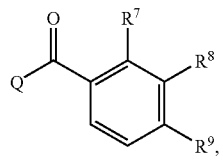

in which
Q is a radical $Q^1$, $Q^2$ or $Q^3$, $Q^1$ 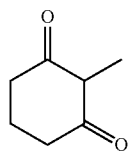

$Q^2$ 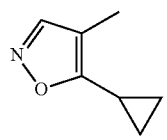

$Q^3$ 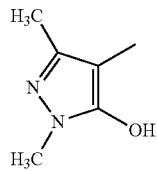

$R^7$ is chlorine, methylsulfonyl or trifluoromethyl,
$R^8$ is hydrogen or 2,2,2-trifluoroethoxymethyl,
$R^9$ is methylsulfonyl or trifluoromethyl.

10. The suspension concentrate as claimed in claim 2, additionally comprising a thixotropic agent.

11. The suspension concentrate as claimed in claim 9, wherein the herbicidally active compound of formula (III) is selected from the group consisting of:

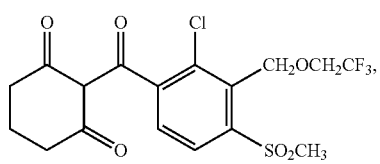

-continued

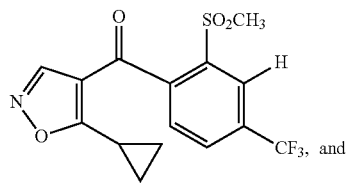

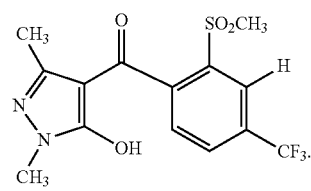

12. The suspension concentrate as claimed in claim 11, comprising
A) from 4 to 30% of said herbicidally active compound of formula (I),
B) from 4 to 30% of said safener of formula (II),
C) from 0 to 35% of said herbicidally active compound of formula (III),
D) from 0.5 to 30% of said dispersants, and
E) from 30 to 70% of said water.

13. The suspension concentrate as claimed in claim 11, comprising
A) from 5 to 25% of said herbicidally active compound of formula (I),
B) from 5 to 25% of said safener of formula (II),
C) from 0 to 30% of said herbicidally active compound of formula (III),
D) from 1 to 20% of said dispersants, and
E) from 35 to 65% of said water.

14. The suspension concentrate as claimed in claim 11, comprising
A) from 5 to 20% of said herbicidally active compound of formula (I),
B) from 8 to 20% of said safener of formula (II),
C) from 0 to 25% of said herbicidally active compound of formula (III),
D) from 2.5 to 15% of said dispersants, and
E) from 40 to 60% of said water.

15. The suspension concentrate as claimed in claim 12, additionally comprising from 1 to 15% of one or more antifreeze agents, from 0.05 to 1% of one or more preservatives, from 0.05 to 1% of one or more defoamers, and from 0.1 to 5% of one or more thickeners or thixotropic agents.

16. The suspension concentrate as claimed in claim 13, additionally comprising from 2 to 10% of one or more antifreeze agents, from 0.05 to 0.5% of one or more preservatives, from 0.1 to 1% of one or more defoamers, and from 0.2 to 3% of one or more thickeners or thixotropic agents.

17. The suspension concentrate as claimed in claim 14, additionally comprising from 2 to 10% of one or more antifreeze agents, from 0.05 to 0.25% of one or more preservatives, from 0.1 to 0.5% of one or more defoamers, and from 0.25 to 2.5% of one or more thickeners or thixotropic agents.

18. The aqueous herbicidal composition as claimed in claim 7, wherein the fertilizer is ammonium sulfate or ammonium nitrate.

* * * * *